(12) United States Patent
Frank et al.

(10) Patent No.: US 8,053,391 B2
(45) Date of Patent: Nov. 8, 2011

(54) RESISTANCE TO ABIOTIC STRESS IN PLANTS

(75) Inventors: Geoff Frank, Nicholasville, KY (US); Nocip Tosun, Izmir (TR)

(73) Assignee: Improcrop U.S.A., Inc., Nicholasville, KY (US)

( * ) Notice: Subject to any disclaimer, the term of this patent is extended or adjusted under 35 U.S.C. 154(b) by 1082 days.

(21) Appl. No.: 11/909,317

(22) PCT Filed: Mar. 31, 2006

(86) PCT No.: PCT/US2006/012257
§ 371 (c)(1),
(2), (4) Date: Sep. 21, 2007

(87) PCT Pub. No.: WO2006/105477
PCT Pub. Date: Oct. 5, 2006

(65) Prior Publication Data
US 2010/0144525 A1      Jun. 10, 2010

Related U.S. Application Data

(60) Provisional application No. 60/755,290, filed on Dec. 30, 2005, provisional application No. 60/666,873, filed on Mar. 31, 2005.

(51) Int. Cl.
*A01N 63/00* (2006.01)
*A01N 63/04* (2006.01)
*A61K 36/06* (2006.01)

(52) U.S. Cl. ............... 504/117; 504/118; 424/93.51; 424/195.16

(58) Field of Classification Search ............. 504/117, 504/118, 643
See application file for complete search history.

(56) References Cited

U.S. PATENT DOCUMENTS

| | | | |
|---|---|---|---|
| 4,551,164 A | 11/1985 | Tenzer | |
| 4,647,537 A | 3/1987 | Shigemitsu | |
| 4,666,497 A | 5/1987 | Tenzer | |
| 5,549,728 A | 8/1996 | Wozniak et al. | |
| 5,639,794 A | 6/1997 | Emerson et al. | |
| 5,686,296 A * | 11/1997 | Hobson et al. ............ | 435/255.1 |
| 5,711,946 A | 1/1998 | Chand-Goyal et al. | |
| 5,876,479 A | 3/1999 | Hedgpeth, IV | |
| 6,214,337 B1 * | 4/2001 | Hayen et al. ............ | 424/93.51 |
| 6,251,951 B1 | 6/2001 | Emerson et al. | |
| 6,318,023 B1 | 11/2001 | Yamashita | |

(Continued)

FOREIGN PATENT DOCUMENTS
WO      WO 03/011310      2/2003

OTHER PUBLICATIONS

U.S. Appl. No. 10/842,267, filed May 10, 2004, Office Action dated Mar. 31, 2008.

(Continued)

*Primary Examiner* — Johann Richter
*Assistant Examiner* — Jane C Oswecki
(74) *Attorney, Agent, or Firm* — King & Schickli, PLLC

(57) ABSTRACT

A method for inducing resistance to abiotic stress is provided, comprising applying to the plant an amount of a composition comprising a yeast cell wall effective to prevent or reduce harmful effects of the pathogen. The composition may further include a plant extract derived from *Yucca*.

19 Claims, 9 Drawing Sheets

U.S. PATENT DOCUMENTS

| | | | |
|---|---|---|---|
| 6,419,922 B1 * | 7/2002 | El Ghaouth et al. | 424/93.51 |
| 6,444,448 B1 * | 9/2002 | Wheatcroft et al. | 435/101 |
| 6,534,446 B1 | 3/2003 | Kinnersley et al. | |
| 7,048,937 B2 * | 5/2006 | Dawson et al. | 424/406 |
| 2003/0064119 A1 | 4/2003 | Emerson | |
| 2003/0068303 A1 | 4/2003 | Selvig et al. | |
| 2004/0156920 A1 | 8/2004 | Kane | |
| 2008/0008767 A1 * | 1/2008 | Duffy et al. | 424/643 |

OTHER PUBLICATIONS

"*Yucca*" (selecting *Yucca baccata*), submitted to Dr. Duke's Phytochemical and Ethnobotanical Databases (http://ars-grin.gov/duke/); submitted May 10, 2007, 6 pps.

Newbold et al.; "Different Strains of *Saccharomyces cerevisiae* Differ in Their Effects on Ruminal Bacterial numbers In Vitro and in Sheep"; J. Anim. Sci. 1995; 73:1811-1818, 8 pps.

* cited by examiner

RESISTANCE TO ABIOTIC STRESS IN PLANTS

This application claims the benefit of U.S. Provisional Patent Application Ser. Nos. 60/666,873 filed Mar. 31, 2005 and 60/755,290 filed Dec. 30, 2005, the disclosures of which are incorporated herein in their entirety by reference.

TECHNICAL FIELD

This invention relates to control of abiotic stress in plants. In particular, the invention relates to methods and compositions for prevention or reduction of harmful effects of abiotic stress such as exposure to high soil salinity. The methods of the invention comprise application of compositions comprising a yeast cell wall preparation to a plant for preventing or reducing harmful effects of abiotic stress.

BACKGROUND OF THE INVENTION

Abiotic stress may be broadly defined as a group of non-living factors, which can result in harmful effects to plants. Examples of abiotic stressors include excessive soil salinity (as well as other adverse soil conditions), drought, high winds, heavy metals, herbicides, and extremes of temperature. Such abiotic stressors may promote the generation of reactive oxygen species in photosynthetic cells, and cell death from abiotic stress may therefore be in part a result of oxidative damage.

As an example, agricultural practices and poor irrigation management in warm and dry regions often result in saline and gypsiferous soils with a low productivity. Indeed, secondary salinization resulting from poor irrigation management affects approximately 20% of irrigated land worldwide. Thus, abiotic stressors such as salt stress represents a serious limitation to soil productivity. Improving crop yields in soils subjected to salinity constraints and other abiotic stressors is a constant goal and need in the art.

A variety of methods have been considered to reduce harmful effects of abiotic stress, including genetic means such as addition of transgenes for antioxidants. Resulting improvements have been limited, however, due to the complexity of the plant antioxidant system, and to the numerous other elements of cell physiology contributing to (or detracting from) stress tolerance. There accordingly remains a need in the art for methods and compositions for improving resistance of plants to abiotic stressors such as high soil salinity. The present invention provides methods for reducing or preventing harmful effects of abiotic stress in plants, comprising application thereto of compositions comprising a yeast cell wall. Application of the compositions of the present invention surprisingly reduces or prevents the harmful effects of abiotic stressors such as high soil salinity in plants.

SUMMARY OF THE INVENTION

In accordance with the purposes of the present invention as described herein, in one aspect of the present invention a method is provided for reducing effects of abiotic stress in a plant, the method comprising applying a composition comprising a yeast cell wall in an amount effective for preventing or reducing harmful effects of the abiotic stress. The composition may comprise at least one yeast-derived mannanoligosaccharide. The composition may be formulated for application as a foliar spray or as a soil drench.

The yeast cell wall of the composition may be derived from a yeast species selected from the group of yeasts consisting of *Saccharomyces*, *Candida*, *Kluyveromyces* and *Torulaspora*. In one embodiment, the yeast cell wall composition may be derived from *Saccharomyces cerevisiae*. In yet another embodiment, the yeast cell wall is derived from *Saccharomyces cerevisiae* strain NCYC 1026. The composition may further comprise at least one plant extract derived from *Yucca*, which may be derived by chopping, crushing, macerating, pressing, or grinding at least a portion of the *Yucca* plant and obtaining a liquid extract therefrom.

The method of the present invention is effective in providing protective effects against a variety of abiotic stressors, including exposure to excessive salinity. The method is effective in providing protective effects for any vegetable crop, forage, fruit crop, orchard crop, or field crop. In one embodiment, the method is practiced on a fruit crop such as a tomato plant.

In another aspect of the present invention, a method is provided for inducing resistance to abiotic stress in a plant, comprising applying a composition comprising a yeast cell wall and at least one plant extract derived from *Yucca* in an amount effective for preventing or reducing harmful effects of the abiotic stress. The yeast cell wall and plant extract may be substantially as described above, and may be formulated as is known in the art for application as a foliar spray or as a soil drench.

It should be appreciated that the embodiments shown and described herein are an illustration of one of the modes best suited to carry out the invention. The skilled artisan will realize that the invention is capable of other different embodiments and its several details are capable of modification in various, obvious aspects all without departing from the invention. Accordingly, the drawings and descriptions will be regarded as illustrative in nature, and not as restrictive.

BRIEF DESCRIPTION OF THE DRAWINGS

The accompanying drawings, which are incorporated in and form a part of the specification, illustrate several aspects of the present invention and together with the description serve to explain the principles of the invention. In the drawings.

Figure 1:
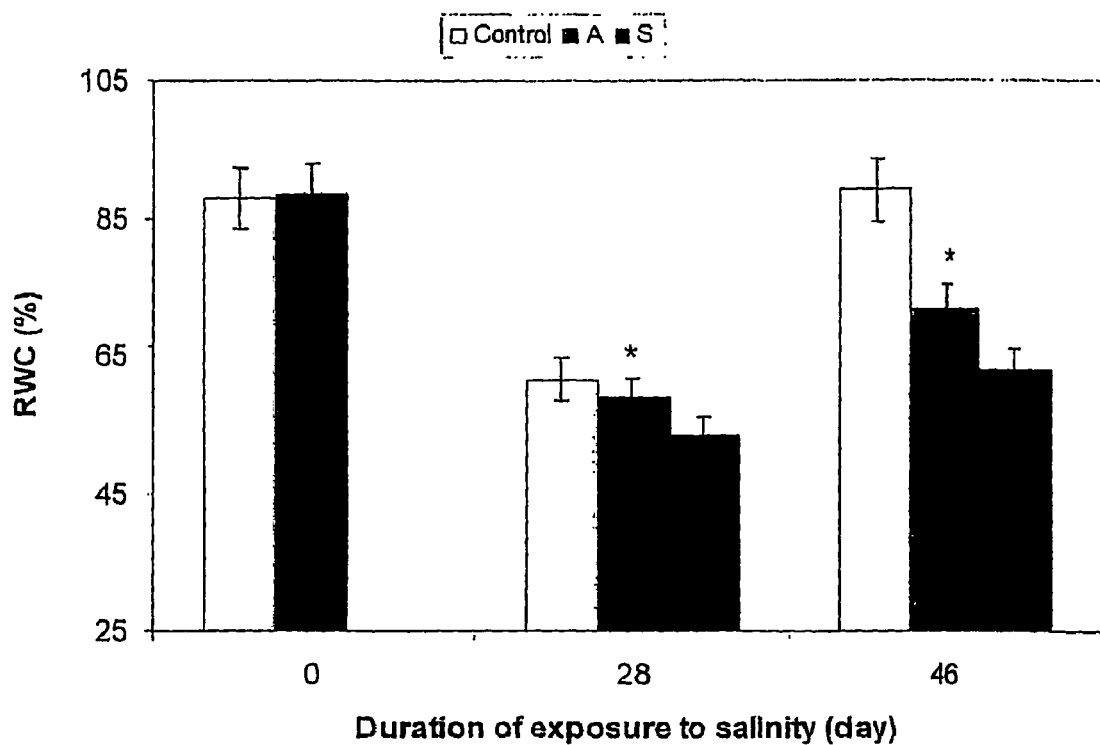
FIG. 1 shows relative water content (RWC) of tomato plant leaves under exposure to salinity (A=yeast cell wall composition plus 100 mM NaCl, S=yeast cell wall composition, *=significantly different from S at $P<0.05$)

Reference will now be made in detail to the present preferred embodiment of the invention, an example of which is illustrated in the accompanying drawings.

DETAILED DESCRIPTION OF THE INVENTION

The following examples are presented in support of and to further illustrate the invention as described herein. However, the invention is not to be considered as limited thereto. The patents, patent applications, and citations of literature referred to herein are understood to form a part of this disclosure, and are incorporated in their entirety by reference.

In accordance with the above identified need in the art, the present invention provides methods for reducing or preventing harmful effects of abiotic stress in plants, comprising application thereto of compositions comprising a yeast cell wall. The composition may further optionally include an extract derived from a *Yucca* plant. Additional methods comprising the composition are described in co-pending U.S. patent application Ser. No. 10/842,267.

At the whole-plant level, abiotic stressors such as Na$^+$ toxicity resulting from excessive soil salinity cause a variety of undesirable effects, including decreased growth rate, leaf damage, and increases in the root to shoot ratio. At the plant tissue/cellular level, effects of excessive soil salinity include water deficit stress, increased concentration of certain ions resulting in metabolic toxicity, and nutritional deficiencies. Many plants respond rapidly to abiotic stresses such as drought and high soil salinity by stomatal closure, which minimizes water loss but also undesirably leads to limited $CO_2$ fixation and reduced NADP$^+$ regeneration.

It is also believed that abiotic stress results in increased plant production of free radicals (reactive oxygen species), disrupting the normal homeostasis between free radical production and detoxification. Reactive oxygen species (ROS) include superoxide radical, hydrogen peroxide, hydroxyl radical, and singlet oxygen. Although these free radicals are normal by-products of processes essential to plant life, they are also highly reactive chemicals that can damage living systems if not rapidly neutralized by the plants antioxidant defense systems. Plant antioxidant defenses can be broadly placed into two categories: (1) antioxidants that react with free radicals and neutralize them, such as peroxidase, superoxide dismutase, and catalase; and (2) antioxidants that regenerate oxidised antioxidants, such as ascorbate peroxidase and glutathione reductase.

It is known to use yeast cell wall and fermentation media-based formulations as plant food compositions. Such compositions provide a variety of useful nutrients for stimulating optimal plant growth and health. It is also known to use yeast-based products for postharvest decay management, which potentially have an effect on fungal growth mediated by competitive inhibition (Wisniewski and Wilson. 1992. Biological control of postharvest diseases of fruits and vegetables: Recent advances. Hort. Science 27: 94-98; Arras et al. 1998. Biocontrol by yeasts of blue mould of citrus fruits and the mode of action of an isolate of *Pichia guilliermondii*. J. Hort. Sci. and Biotechnology 73: 413-418). However, the potential for reduction of abiotic stress using a non-living yeast preparation has not yet been evaluated.

Experimental Procedures

The following experimental procedures apply to the examples disclosed herein.

A. Growth Parameters

Roots and shoots of harvested plants were separated, and lengths and fresh weights were measured. Root and shoot dry weights were determined after oven drying at 70° C. for 3 days.

B. Leaf Relative Water Content (RWC)

Leaf relative water content was determined by measuring fresh weights (FW) of six leaf disks from each experimental group. The disks were then floated on deionized water under low irradiance for 7 hr, to determine turgid weight (TW). The leaf samples were then oven dried at 70° C. for 3 days to determine dry weight (DW). Leaf RWC was calculated in accordance with the formula:

$$RWC(\%)=[FW-DW)/(TW-DW)]\times 100$$

C. Stomatal Conductance

Stomatal conductance was measured on fully expanded intact leaves using a portable porometer.

D. Chlorophyll Fluorescence

Photosynthetic efficiency of photosystem II (PS II) was measured with a portable plant efficiency analyzer (HANSATECH Inst. Ltd., Norfolk, UK). Fv/Fm ratios were calculated to compare to the photosynthetic efficiency of PS II.

E. Antioxidant Enzyme Activities

Leaf samples were homogenized in ice cold 50 mM sodium phosphate buffer (pH 7.8) containing 1 mM EDTA.Na$_2$ and 5% (w/v) insoluble PVPP at 0-4° C. Homogenates were centrifuged (13,000×g for 20 min at 0° C.), and enzymatic activity of the supernatant was measured. Superoxide dismutase (SOD; EC 1.15.1.1) activity was measured spectrophotometrically (Beauchamp, C., and Fridovich, I. 1971. Superoxide dismutase: Improved assays and an assay applicable to acrylamide gels. *Anal. Biochem.* 44: 276-287).

Peroxidase (POX; EC 1.11.1.7) was determined according to Herzog and Fahimi (Herzog, V., Fahimi, H. 1973. Determination of the activity of peroxidase. *Anal. Biochem.* 55: 554-562). Ascorbate peroxidase (AP; EC 1.11.1.11) was estimated according to Nakano and Asada (Nakano, Y., Asada, K. 1981. Hydrogen peroxide is scavenged by ascorbate specific peroxidase in spinach chloroplast. *Plant Cell Physiol.* 22: 867-880). Catalase (CAT; EC 1.11.1.6) was assayed by measuring the initial rate of disappearance of peroxide (Bergmeyer, N. 1970. Methoden der enzymatishcen Analyse. Akademie Verlag, Berlin. Vol. 1, pp 636-647). Glutathione reductase (GR; EC 1.6.4.2) was measured according to Foyer and Halliwell (Foyer, C. H., Halliwell, B. 1976. The presence of glutathione and glutathione reductase in chloroplasts: a proposed role in ascorbic acid metabolism. *Planta* 133: 21-25).

F. Lipid Peroxidation

The level of lipid peroxidation was determined in terms of malondialdehyde (MDA) content using a thiobarbituric acid method [Madhava, Rao, K. V., Sresty, T. V. S. 2000. Antioxidative parameters in the seedlings of pigeonpea (*Cajanus cajan* L. Millspaugh) in response to Zn and Ni stresses. *Plant Sci.* 157: 113-128).

G. Proline Content

Proline level was determined according to Bates et al. (Bates, L. S., Waldren, R. P., Teare, I. D. 1973. Rapid determination of free proline for water-stress studies. *Plant Soil* 39: 205-207).

Example 1

Leaves of 2-week old tomato seedlings were exposed to salt stress. The leaves were sprayed for a 4 week period with either distilled water (as a control) or distilled water containing a 0.5% (v/v) solution of a composition comprising 300 mg/L yeast cell wall (2.0-3.0% v/v), derived from *Saccharomyces cerevisiae* strain NCYC 1026. The composition further included 29.5-31.0% (v/v) *Yucca* extract, derived by macerating the bark of the *Yucca* plant and obtaining a juice therefrom. The remainder of the composition comprised spent bacterial fermentation media (65-67% v/v), sodium benzoate (0.03-0.4% v/v), and potassium sorbate (0.1-0.2% v/v).

After treatment with either distilled water or the composition of the present invention for the 4 week period, the seedlings were exposed to 100 mM NaCl for a 6 week period. Leaf samples were obtained on day 0, 28, and 43 after initiation of salt stress, and stored at −20° C. until analyzed. At the same time periods, measurements of various growth parameters were obtained as described previously.

The yeast cell wall composition had no significant effect on tomato root and shoot length in plants exposed to salt stress (data not shown). As shown in Table 1, the effects of salt stress on shoot fresh weight, shoot dry weight, and root dry weight were alleviated by the composition of this invention.

TABLE 1

Tomato plant root and shoot weight following salt stress.

| Day | Control | Yeast cell wall + NaCl | NaCl |
|---|---|---|---|
| Shoot fresh weight (g) | | | |
| 0 | 9.38 ± 1.83 | 9.00 ± 0.25 | — |
| 28 | 25.35 ± 2.91 | 17.75 ± 4.45 | 16.38 ± 2.41 |
| 43 | 26.29 ± 2.02 | 20.07 ± 3.12 | 15.84 ± 3.15 |
| Shoot dry weight (g) | | | |
| 0 | 0.778 ± 0.02 | 0.658 ± 0.06 | — |
| 28 | 2.957 ± 0.04 | 2.805 ± 0.09 | 2.540 ± 0.08 |
| 43 | 3.368 ± 0.09 | 3.292 ± 0.07 | 3.187 ± 0.08 |
| Root fresh weight (g) | | | |
| 0 | 2.60 ± 0.25 | 2.12 ± 0.37 | — |
| 28 | 3.69 ± 0.75 | 4.37 ± 0.42 | 4.27 ± 0.72 |
| 43 | 5.87 ± 0.96 | 4.57 ± 0.77 | 4.85 ± 0.89 |
| Root dry weight (g) | | | |
| 0 | 0.172 ± 0.028 | 0.158 ± 0.027 | — |
| 28 | 0.626 ± 0.041 | 0.488 ± 0.056 | 0.461 ± 0.061 |
| 43 | 0.540 ± 0.040 | 0.572 ± 0.069 | 0.428 ± 0.036 |

Application of the yeast cell wall composition of the invention, significantly improved shoot dry weight of tomatoes under high soil salinity conditions at day 28, and similarly improved shoot fresh weight at day 43. Similarly, the composition of the present invention alleviated effects of salinity on tomato plant root dry weight. Accordingly, a positive effect of the present method on growth parameters of treated plants was seen in the presence of salt stress.

Figure 2:
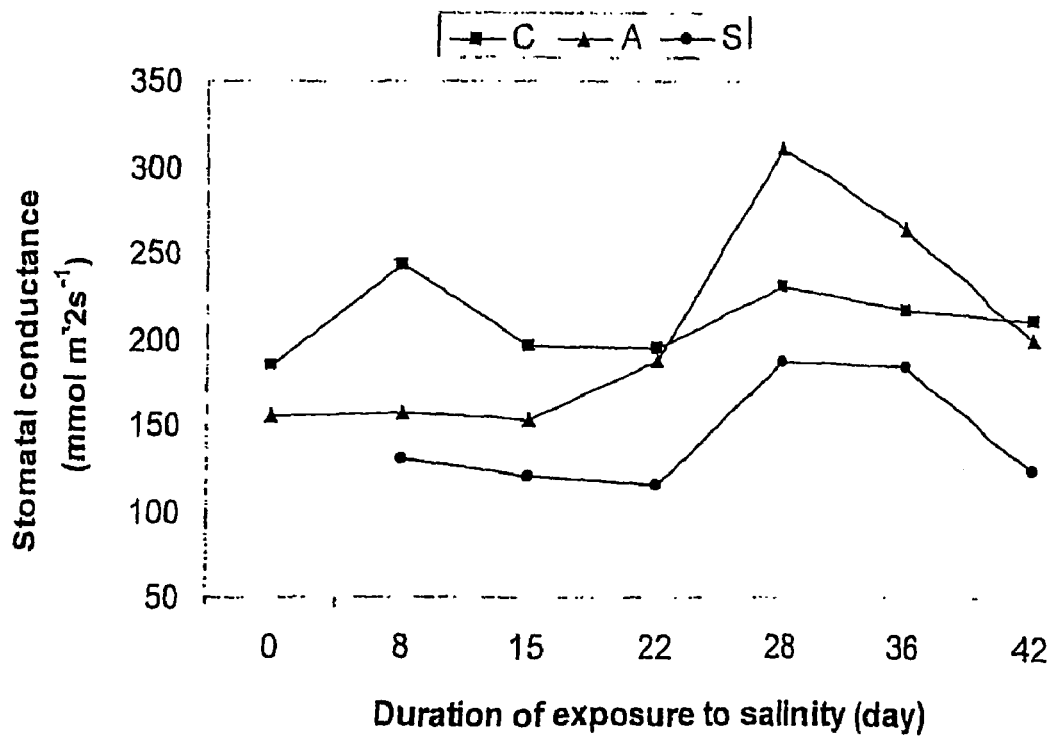
FIG. 2 shows stomatal conductance of tomato plant leaves during exposure to saline.
Figure 3:
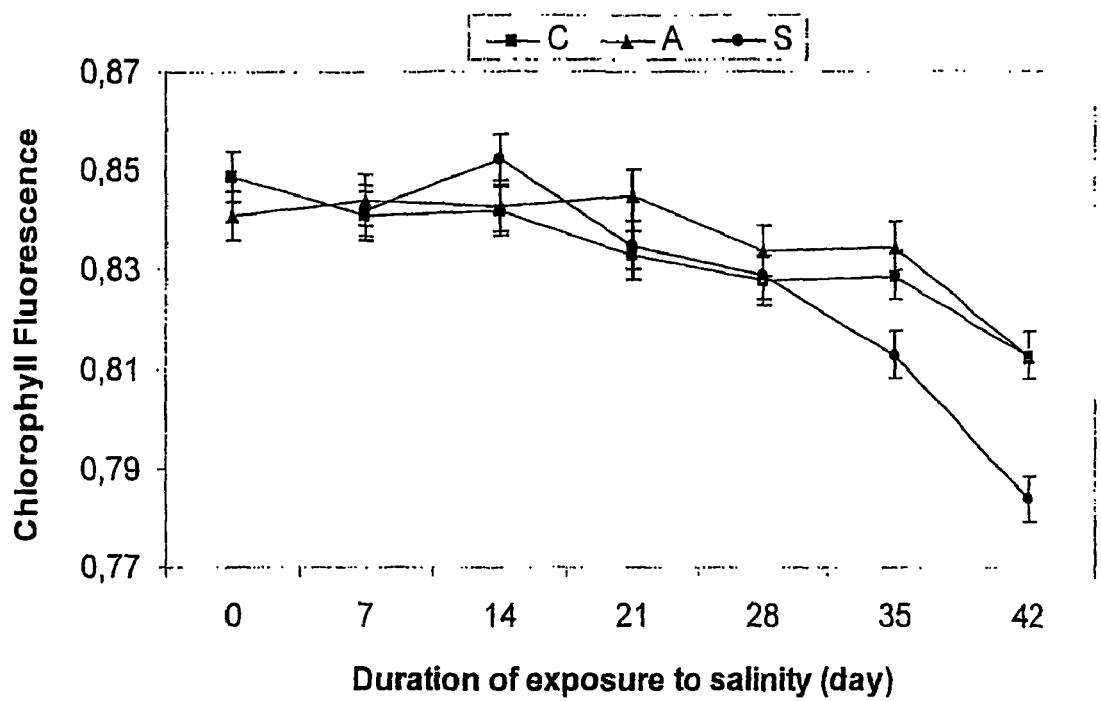
FIG. 3 shows chlorophyll fluorescence (Fv/Fm ratios) during salt stress, demonstrating the protective effect of the present yeast cell wall composition during salt stress.
Figure 4:
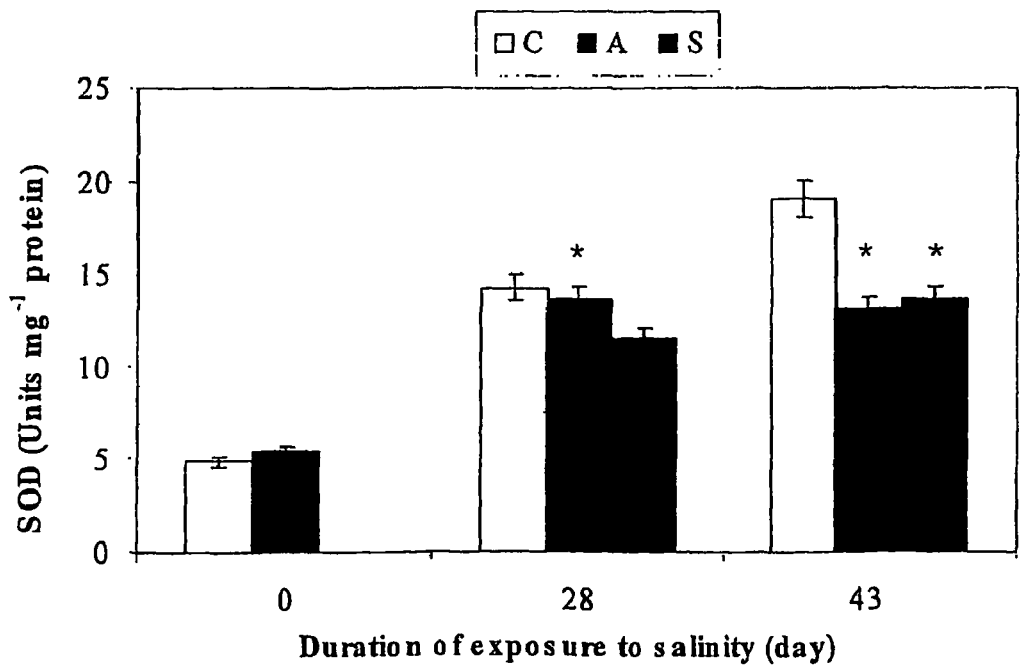
FIG. 4 shows superoxide dismutase (SOD) activity in tomato plant leaves during salt stress, and demonstrates a significant increase in SOD activity in leaves treated with the yeast cell wall composition compared to salt-stressed leaves alone ($P<0.05$)
Figure 5:
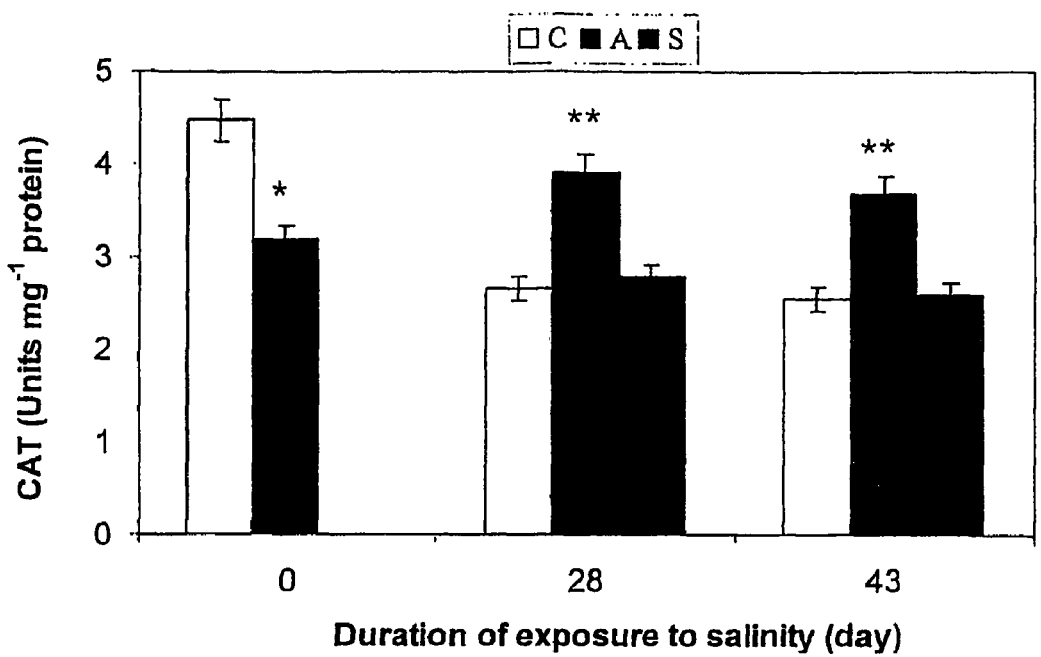
FIG. 5 shows catalase (CAT) activity in tomato plant leaves during salt stress, and shows an increase in CAT activity in leaves treated with the composition of the present invention.
Figure 6:
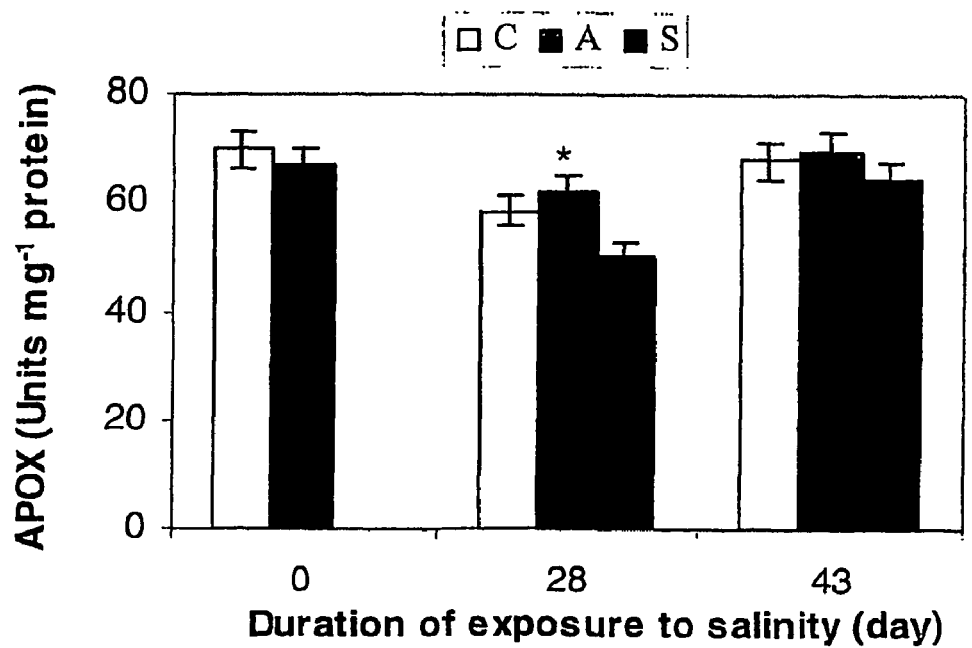
FIG. 6 shows ascorbate peroxidase (AP) activity in tomato plant leaves during salt stress, and shows an increase in AP activity with application of the yeast cell wall composition on day 28 of salt stress.
Figure 7:
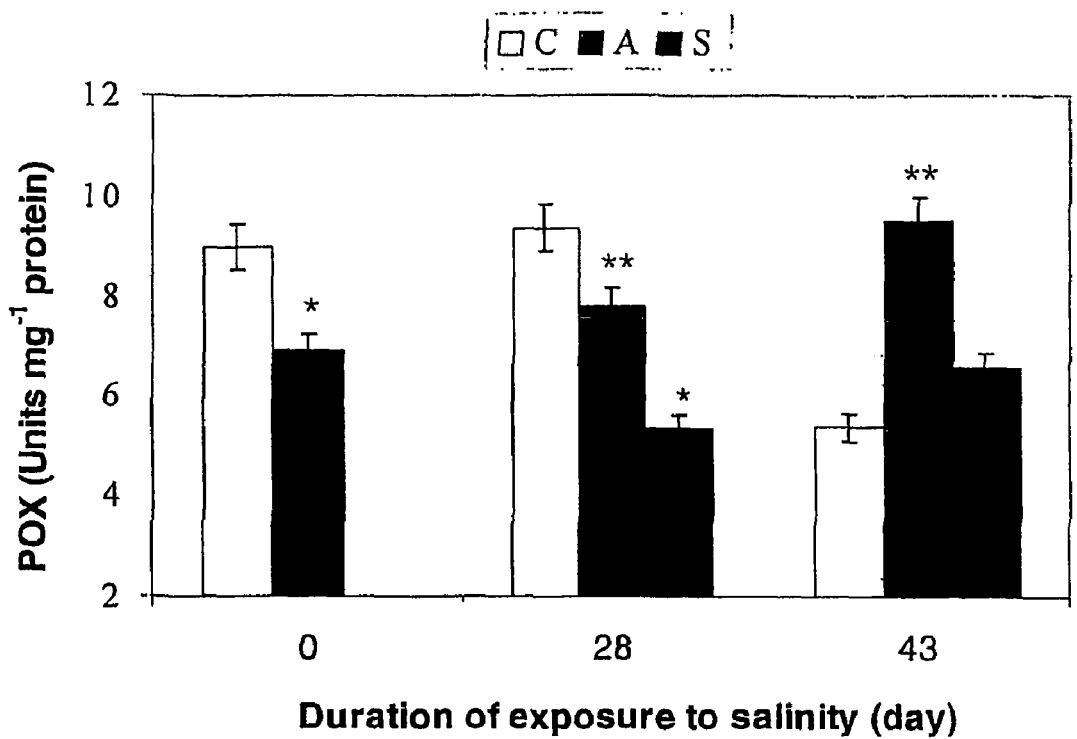
FIG. 7 shows an improvement in peroxidase (POX) activity in salt-stressed leaves treated with the present composition compared to salt-stressed leaves.
Figure 8:
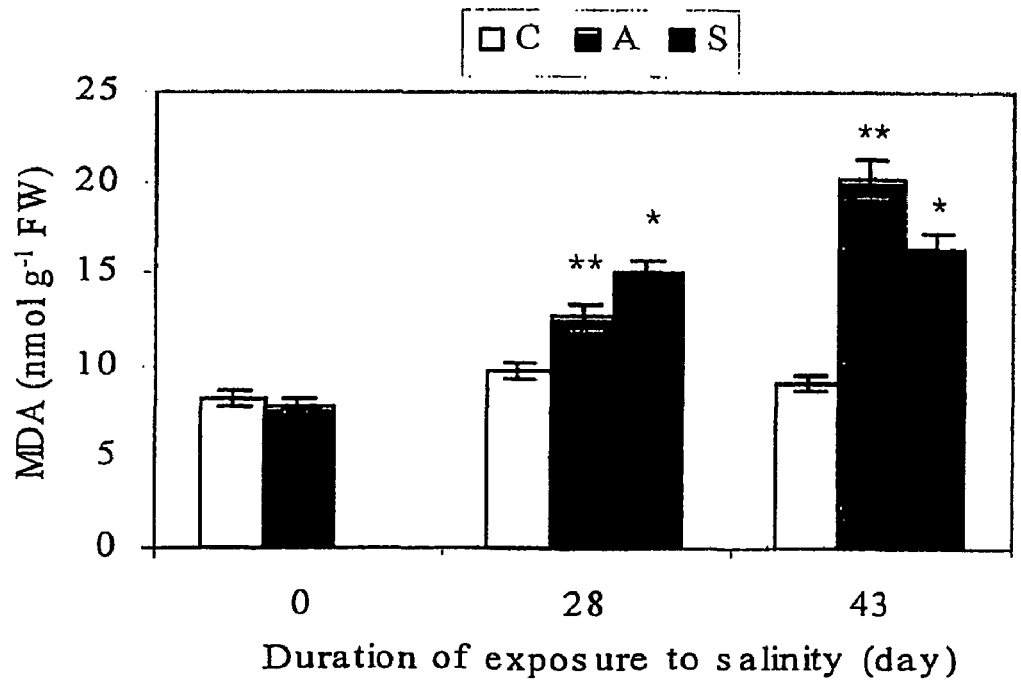
FIG. 8 shows a reduction in the impact of NaCl stress on tomato plant lipid peroxidation (malondialdehyde, MDA) by application of the present composition.

With reference to the Figures, the composition of the present invention was protective against the decrease in leaf RWC stimulated by salt stress (FIG. 1). Protection against salinity-induced reduction in leaf water content was therefore shown. Similarly, stomatal conductivity (FIG. 2), chlorophyll fluorescence (FIG. 3), SOD (FIG. 4), catalase (a hydrogen peroxide detoxifier; FIG. 5) ascorbate peroxidase (FIG. 6), peroxidase (FIG. 7), and lipid peroxidation (FIG. 8) were negatively impacted by salt stress. The method of the present invention was uniformly protective against the decreases in these measures of plant stress caused by salt stress.

It is accordingly shown that the method of the present invention effectively reduced decreases in root and shoot dry weight caused by excessive soil salinity. The method further enhanced water retaining capacity, and protected the turgor of the plants against dehydration induced by such soil salinity. Stomatal closing in response to salt stress was suppressed, suggesting that plant $CO_2$ uptake could be maintained even under such conditions of stress. The decrease in photoinhibition in PS II efficiency caused by soil salinity was reduced. Further, activity of various enzymes involved in detoxification of free radicals or in regeneration of free-radical detoxifying enzymes was preserved even under salt stress by the method of this invention, showing that the plants so treated were capable of maintaining more normal function even when exposed to excessive soil salinity. Accordingly, an effective method for providing total plant protection for plants under abiotic stressors such as soil salinity is provided.

Example 2

F1 hybrid tomato plants (*Lycopersicon esculentum* Mill cv. Zeraim Gedera) were grown in a greenhouse at 20-25° C. under natural light in standard potting compost in 19 cm diameter pots. At three weeks of age, seedlings were sprayed to runoff with a control (distilled water) or the composition as described in Example 1 (600, 1200, and 1800 µl $L^{-1}$) once weekly. Beginning at four weeks of age, the seedlings were then irrigated with 35 mM, 70 mM, or 140 mM NaCl twice a week, and this treatment was continued through 10 weeks from initiation of salt treatment. The plants were harvested at the described intervals, and physiological measurements were taken and antioxidant enzyme activities determined as described above.

Figure 9:
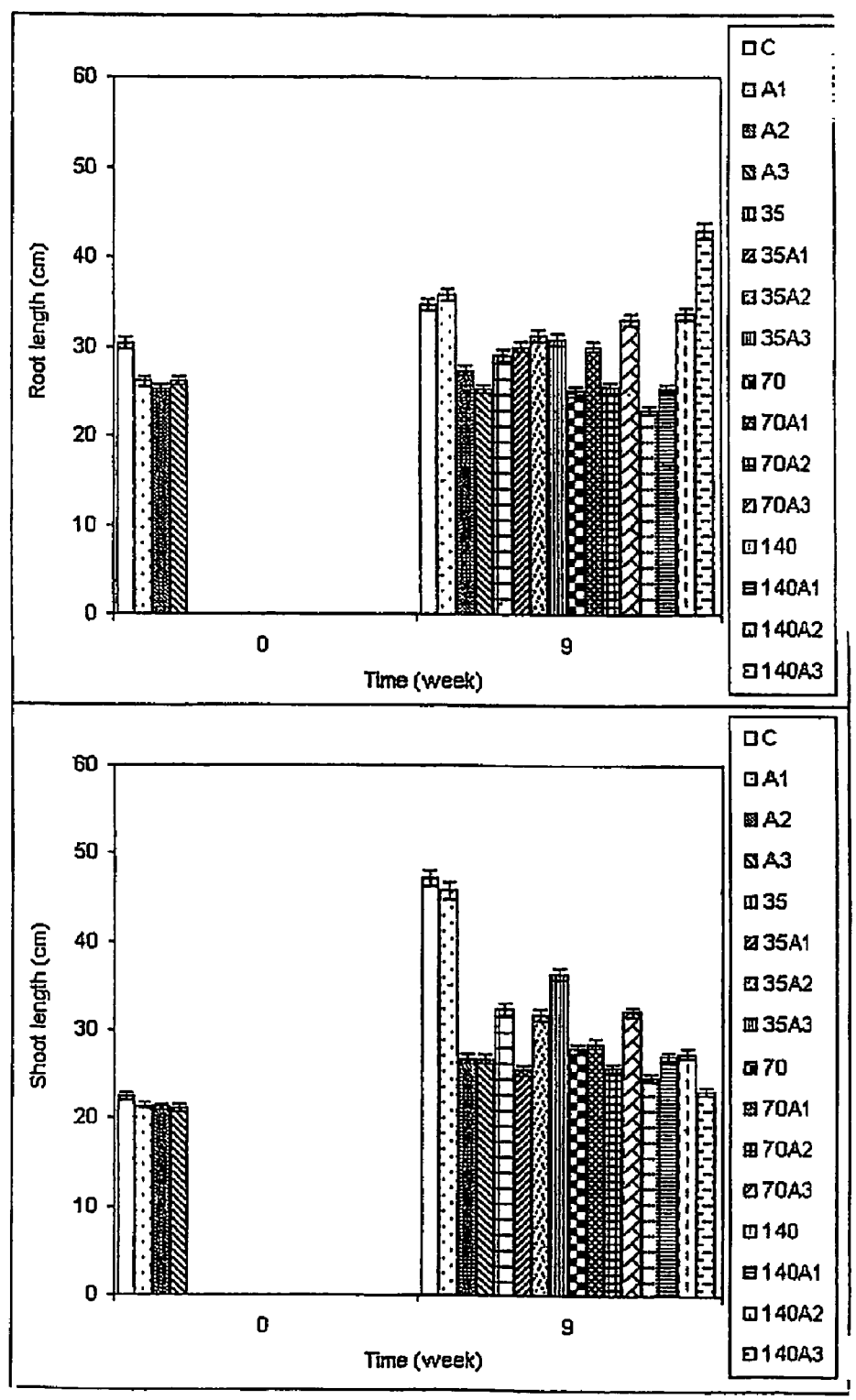
FIG. 9 depicts root and shoot length of tomato plants exposed to varying levels of salt stress (C=distilled water control; A1=yeast cell wall composition at 600 μl L$^{-1}$; A2=yeast cell wall composition at 1200 μl L$^{-1}$; A3=yeast cell wall composition at 1800 μl L$^{-1}$; 35=35 mM NaCl; 35A1=yeast cell wall composition at 600 μl L$^{-1}$+35 mM NaCl; 35A2=yeast cell wall composition at 1200 μl L$^{-1}$+35 mM NaCl; 35A3=yeast cell wall composition at 1800 μl L$^{-1}$+35 mM NaCl; 70=70 mM NaCl; 70A1=yeast cell wall composition at 600 μl L$^{-1}$+70 mM NaCl; 70A2=yeast cell wall composition at 1200 μl L$^{-1}$+70 mM NaCl; 70A3=yeast cell wall composition at 1800 μl L$^{-1}$+70 mM NaCl; 140=140 mM NaCl; 140A1=yeast cell wall composition at 600 μl L$^{-1}$+140 mM NaCl; 140A2=yeast cell wall composition at 1200 μl L$^{-1}$+140 mM NaCl; 140A3=yeast cell wall composition at 1800 μl L$^{-1}$+140 mM NaCl)
Figure 10:
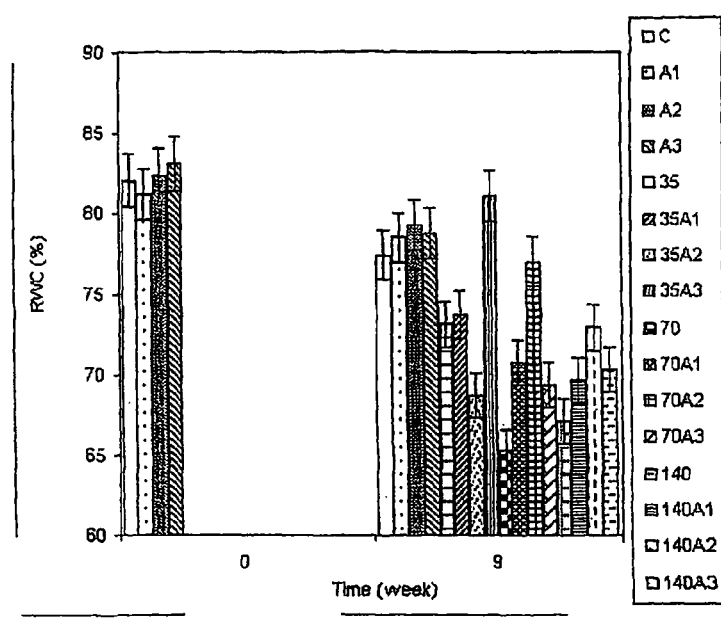
FIG. 10 depicts RWC of tomato plants exposed to varying levels of salt stress (35, 70, 140 mM NaCl)
Figure 11:
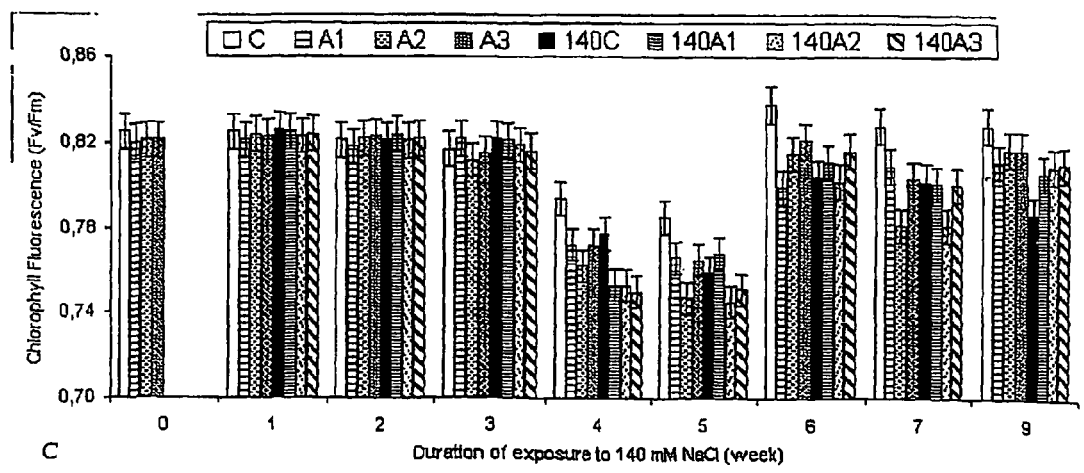
FIG. 11 depicts photosynthetic efficiency (Fv/Fm) of tomato plants exposed to 140 mM NaCl.

As shown in FIG. 9, root and shoot length of the plants decreased with increasing salinity by the ninth week of treatment. The composition of the present invention increased root and shoot length of salt-stressed plants at the higher concentrations (1200 and 1800 µl L$^{-1}$) and the higher levels of salt (70 and 140 mM NaCl). Similarly (see FIG. 10), leaf RWC decreased significantly under 70 and 140 mM NaCl stress. Application of the composition of the present invention ameliorated the reduction in leaf RWC observed over application of NaCl alone, indicating a reduction in salinity-induced water losses. Chlorophyll fluorescence, i.e., photosynthetic efficiency of PS II (Fv/Fm ratio) during salt stress is shown in FIG. 11. Improvements in protection were observed with application of the composition of the present invention by week 9 of treatment, particularly at the highest concentration of salt (140 mM NaCl) applied, showing that the present method improved photosynthetic efficiency in plants under conditions of salt stress.

Figure 12:
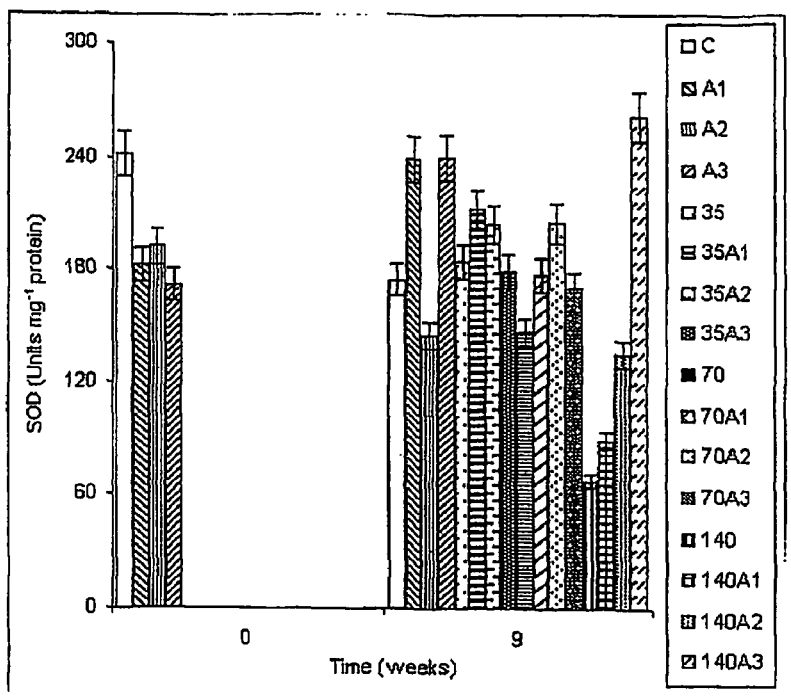
FIG. 12 shows SOD activity in tomato plant leaves at varying levels of salt stress (35, 70, 140 mM NaCl)
Figure 13:
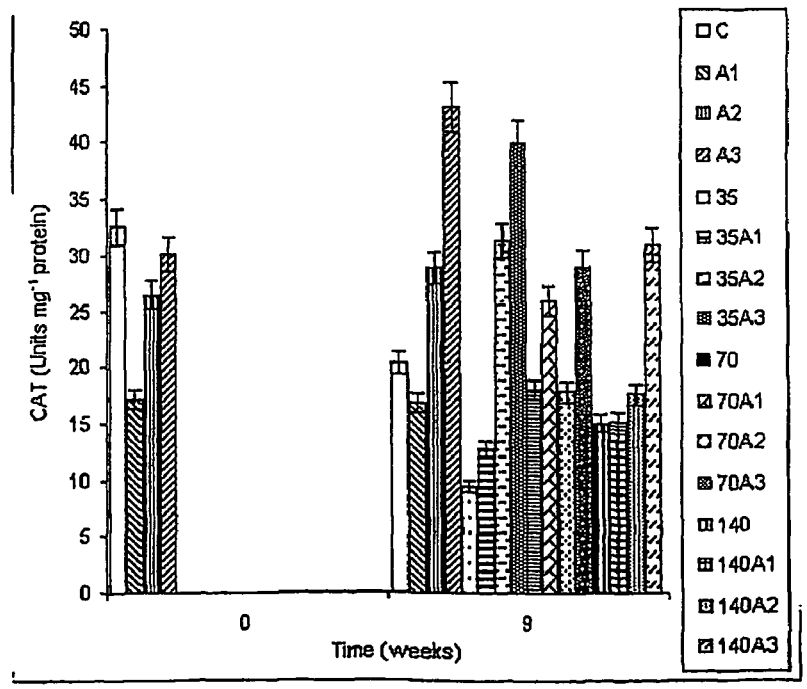
FIG. 13 shows CAT activity in tomato plant leaves at varying levels of salt stress (35, 70, 140 mM NaCl)

Turning to the data for plant antioxidant systems, activity of SOD, a scavenger of superoxide radical, is shown in FIG. 12. Activity of SOD decreased with increasing salinity in comparison to controls, particularly at the 140 mM concentration of NaCl. The composition of the present invention enhanced SOD activity, particularly at the highest concentrations. Similarly (see FIG. 13), the present composition at 1200 and 1800 µl L$^{-1}$ enhanced CAT activity at 9 weeks following application of 35 mM NaCl. Catalase is important because it eliminates $H_2O_2$ produced by SOD. The present composition at 600 and 1200 µl L$^{-1}$ enhanced CAT activity at 9 weeks following application of 70 mM NaCl. Application of the present composition at 1800 µl L$^{-1}$ enhanced CAT activity at 9 weeks following application of 140 mM NaCl to levels greater than the control group.

Figure 14:
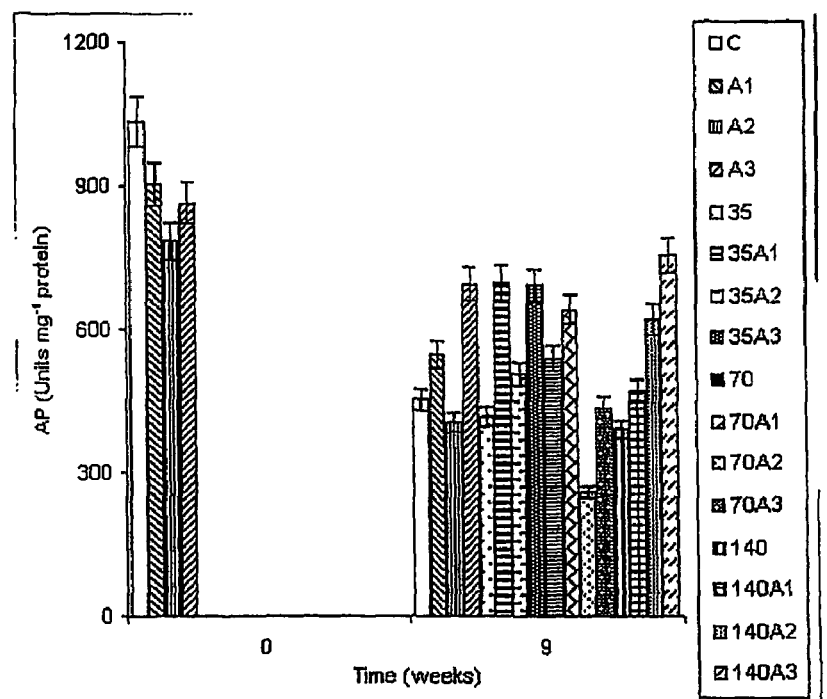
FIG. 14 shows AP activity in tomato plant leaves at varying levels of salt stress (35, 70, 140 mM NaCl)

Similarly, the composition of the present invention enhanced AP (which together with monodehydroascorbate reductase, dehydroascorbate reductase, and glutathione reductase aid in removing $H_2O$; see Foyer and Halliwell, 1976) and GR activity in salt-stressed tomato plants. In particular (see FIG. 14), AP activity in plants exposed to 35 and 70 mM NaCl was increased by application of the present composition. The observed increase was greatest in plants exposed to 140 mM NaCl and 1200 and 1800 µl L$^{-1}$ of the present composition, reaching an activity level greater than the control group.

Figure 15:
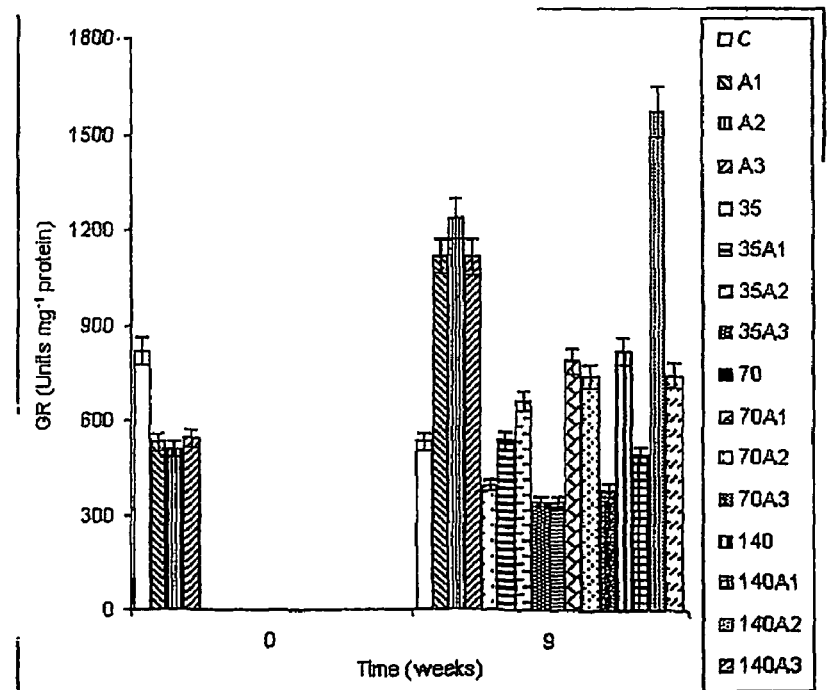
FIG. 15 shows glutathione reductase (GR) activity in tomato plant leaves at varying levels of salt stress (35, 70, 140 mM NaCl)
Figure 16:
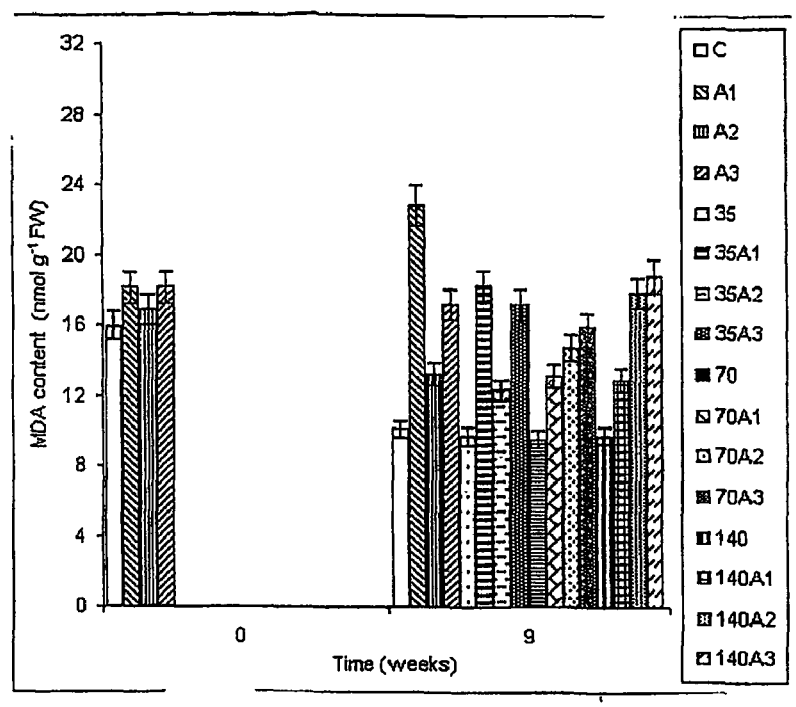
FIG. 16 depicts MDA content in tomato plant leaves at varying levels of salt stress (35, 70, 140 mM NaCl)
Figure 17:
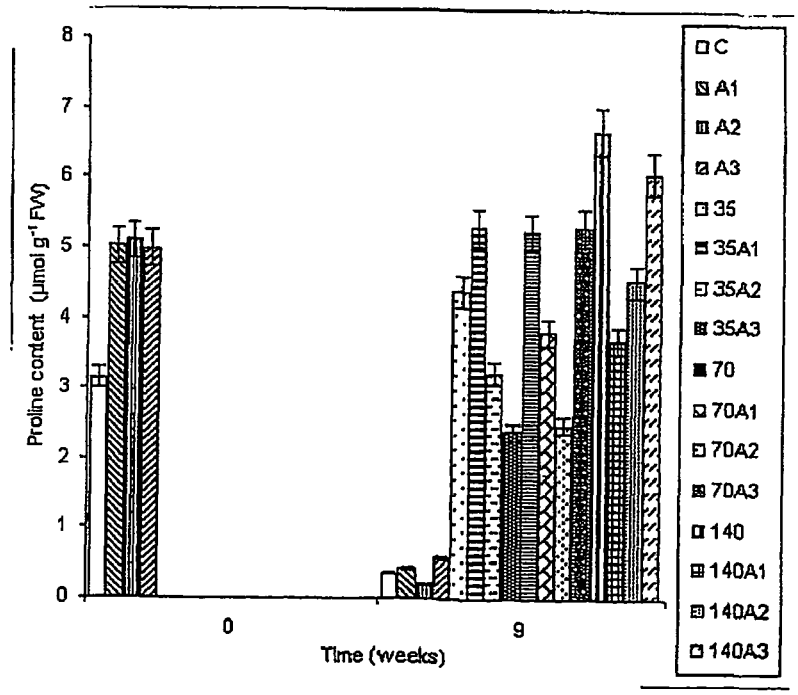
FIG. 17 depicts proline content in tomato plant leaves at varying levels of salt stress (35, 70, 140 mM NaCl).

The composition of the present invention (600 and 1200 µl L$^{-1}$; see FIG. 15) also increased GR activity, particularly in tomato plant leaves exposed to 35 and 70 mM. Malondialdehyde (a measure of lipid peroxidation) in tomato plant leaves was decreased by salt stress (FIG. 16). Lipid peroxidation reflects free radical-induced oxidative damage at the cellular level. All levels of application of the present composition increased MDA level of tomato plants under each condition of salinity evaluated.

Proline is considered a carbon and nitrogen source for rapid plant recovery from stress and growth, a stabilizer for membranes and certain macromolecules, a free radical scavenger, as a pool for energy to regulate redox potential, and as a regulator for cytosolic pH (Jain, M., Mathur, G., Koul, S., Sarin, N. B. 2001. Ameliorative effects of proline on salt stress-induced lipid peroxidation in cell lines of groundnut (*Arachis hypogea* L.). *Plant Cell Rep.* 20: 463-468). Proline accumulation increased significantly with increasing salinity concentration at 9 weeks of treatment. The present composition caused remarkable increases in proline content of tomato plants subjected to the lowest concentration of salt (35 mM).

It is accordingly shown herein that the method of the present invention provided enhanced protection, particularly under conditions of medium and high levels of soil salinity (70 and 140 mM NaCl). The method resulted in enhanced activities of various antioxidant enzymes under differing levels of salinity. Similarly, vegetative growth of plants under conditions of excess salinity was improved.

The foregoing description of the preferred embodiment of this invention has been presented for purposes of illustration and description. It is not intended to be exhaustive or to limit the invention to the precise form disclosed. Obvious modifications or variations are possible in light of the above teachings. For example, additional nutrients or sources of nutrients such as trace minerals, vitamins, sugar sources such as molasses, and the like could be added to supply additional benefits to the treated plant. Still further, known beneficial organisms such as Lactobacilli could be added to include a competitive inhibitory effect against growth of plant pathogens. Alternative preservatives could be added to extend shelf life.

The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for reducing effects of abiotic stress in a plant, the method comprising applying a composition comprising a yeast cell wall in an amount effective for preventing or reducing harmful effects of the abiotic stress.

2. The method of claim 1, wherein the composition comprises at least one yeast-derived mannanoligosaccharide.

3. The method of claim 1, wherein the composition is formulated for application as a foliar spray or as a soil drench.

4. The method of claim 1, wherein the composition is derived from a yeast species selected from the group of yeasts consisting of *Saccharomyces, Candida, Kluyveromyces* and *Torulaspora*.

5. The method of claim 4, wherein the composition is derived from *Saccharomyces cerevisiae*.

6. The method of claim 5, wherein the composition is derived from *Saccharomyces cerevisiae* strain NCYC 1026.

7. The method of claim 1, wherein the composition further comprises at least one plant extract derived from *Yucca*.

8. The method of claim 7, wherein the plant extract is derived by chopping, crushing, macerating, pressing, or grinding said *Yucca* plant and obtaining a liquid extract therefrom.

9. The method of claim 1, wherein the abiotic stress is exposure to excessive salinity.

10. The method of claim 1, wherein the plant is a tomato plant.

11. A method for inducing resistance to abiotic stress in a plant, comprising applying a composition comprising a yeast cell wall and at least one plant extract derived from *Yucca* in an amount effective for preventing or reducing harmful effects of the abiotic stress.

12. The method of claim 11, wherein the composition includes at least one yeast-derived mannanoligosaccharide.

13. The method of claim 11, wherein the composition is formulated for application as a foliar spray or as a soil drench.

14. The method of claim 11, wherein the yeast cell wall is derived from a species selected from the group consisting of *Saccharomyces, Candida, Kluyveromyces* and *Torulaspora*.

15. The method of claim 14, wherein the yeast cell wall is derived from *Saccharomyces cerevisiae*.

16. The method of claim 15, wherein the yeast cell wall is derived from *Saccharomyces cerevisiae* strain NCYC 1026.

17. The method of claim 11, wherein the plant extract is derived by chopping, crushing, macerating, pressing, or grinding the *Yucca* plant and obtaining a liquid extract therefrom.

18. The method of claim 11, wherein the abiotic stress is exposure to excessive salinity.

19. The method of claim 11, wherein the plant is a tomato plant.

* * * * *